United States Patent
Jahns

(10) Patent No.: US 11,969,488 B2
(45) Date of Patent: Apr. 30, 2024

(54) STORAGE STABLE GLASS IONOMER COMPOSITION AND USE THEREOF

(71) Applicant: 3M INNOVATIVE PROPERTIES COMPANY, St. Paul, MN (US)

(72) Inventor: Michael Jahns, Gilching (DE)

(73) Assignee: Solventum Intellectual Properties Company, St. Paul, MN (US)

( * ) Notice: Subject to any disclaimer, the term of this patent is extended or adjusted under 35 U.S.C. 154(b) by 801 days.

(21) Appl. No.: 16/981,733

(22) PCT Filed: Mar. 27, 2019

(86) PCT No.: PCT/IB2019/052497
§ 371 (c)(1),
(2) Date: Sep. 17, 2020

(87) PCT Pub. No.: WO2019/193459
PCT Pub. Date: Oct. 10, 2019

(65) Prior Publication Data
US 2021/0361535 A1    Nov. 25, 2021

(30) Foreign Application Priority Data
Apr. 3, 2018 (EP) .................... 18165371

(51) Int. Cl.
A61K 6/889    (2020.01)
A61K 6/15    (2020.01)
A61K 6/61    (2020.01)
A61K 6/75    (2020.01)
A61K 6/76    (2020.01)
A61K 6/77    (2020.01)

(52) U.S. Cl.
CPC .............. *A61K 6/889* (2020.01); *A61K 6/15* (2020.01); *A61K 6/61* (2020.01); *A61K 6/75* (2020.01); *A61K 6/76* (2020.01); *A61K 6/77* (2020.01)

(58) Field of Classification Search
CPC . A61K 6/889; A61K 6/15; A61K 6/61; A61K 6/75; A61K 6/76; A61K 6/77; A61K 6/60
See application file for complete search history.

(56) References Cited

U.S. PATENT DOCUMENTS

| | | | | |
|---|---|---|---|---|
| 4,209,434 A | * | 6/1980 | Wilson | A61K 6/889 106/35 |
| 4,360,605 A | * | 11/1982 | Schmitt | A61K 6/889 524/559 |
| 4,569,954 A | * | 2/1986 | Wilson | A61K 6/889 106/35 |
| 5,918,772 A | | 7/1999 | Keller | |
| 5,944,419 A | | 8/1999 | Streiff | |
| 2003/0136303 A1 | * | 7/2003 | Kobayashi | C04B 28/28 106/35 |
| 2006/0187752 A1 | | 8/2006 | Keller | |
| 2007/0090079 A1 | | 4/2007 | Keller | |
| 2007/0173568 A1 | * | 7/2007 | Nishikawa | C04B 24/267 524/556 |
| 2008/0027177 A1 | * | 1/2008 | Nishikawa | C04B 40/0039 525/170 |

FOREIGN PATENT DOCUMENTS

| | | | |
|---|---|---|---|
| EP | 1319386 | 6/2003 | |
| EP | 2163233 | 3/2010 | |
| EP | 3100712 | 12/2016 | |
| GB | 2021123 | 11/1979 | |
| WO | WO 2001-049251 | 7/2001 | |
| WO | WO-0149251 A1 * | 7/2001 | .......... A61K 6/0835 |
| WO | WO 2005-016783 | 2/2005 | |
| WO | WO 2007-104037 | 9/2007 | |
| WO | WO 2009-061884 | 5/2009 | |
| WO | WO 2010-123800 | 10/2010 | |
| WO | WO 2015-115597 | 8/2015 | |
| WO | WO 2017-015193 | 1/2017 | |

OTHER PUBLICATIONS

International Search Report for PCT International Application No. PCT/IB2019/052497, dated Jul. 12, 2019, 4 pages.

* cited by examiner

*Primary Examiner* — Peter A Salamon
(74) *Attorney, Agent, or Firm* — Kevin Weber

(57) ABSTRACT

The invention relates to a kit of parts for preparing a glass ionomer composition for dental use, the kit comprising a Paste A and a Paste B, Paste A comprising water, acid-reactive inorganic filler A, non acid-reactive filler B1, sugar alcohol with 6 hydroxyl moieties, Paste B comprising water, polyacid, non acid-reactive filler B2, the sugar alcohol being present in an amount of not more than 2 wt. % and the water being present in an amount of not more than 15 wt. %, wt. % with respect to the whole composition obtained when mixing Paste A and Paste B.
The invention also relates to a hardened glass ionomer composition for dental use obtained by mixing Paste A and Paste B of the kit of parts.

16 Claims, No Drawings

STORAGE STABLE GLASS IONOMER COMPOSITION AND USE THEREOF

CROSS REFERENCE TO RELATED APPLICATIONS

This application is a national stage filing under 35 U.S.C. 371 of PCT/IB2019/052497, filed Mar. 27, 2019, which claims the benefit of European Application No. 18165371.8, filed Apr. 30, 2018, the disclosure of which is incorporated by reference in its/their entirety herein.

FIELD OF THE INVENTION

The invention relates to a glass ionomer cement which can be obtained from a kit of parts containing two pastes to be mixed, wherein one paste contains a sugar alcohol. The kit of parts has improved storage stability and handling properties and the glass ionomer cement obtained after hardening shows good mechanical properties.

BACKGROUND

Conventional glass ionomer compositions are typically offered in form of a powder/liquid system.

These glass ionomer compositions contain as mandatory components a polyacid, an acid-reactive glass and water.

However, the mixing of the ionomer glass (powder) and the polyacid solution (liquid) to obtain a homogeneous material is often challenging for practitioners. Further, depending on the production process, there might be additional material defects (e.g. powder agglomerates or air inclusions). Thus, glass ionomer composition in the form of a paste/paste system have been suggested.

Providing a glass ionomer composition as a paste/paste system is very comfortable for the operator.

However, conventional glass ionomer compositions in paste/paste form contain water as the only solvent. It has been proven quite challenging to ensure stability of such pastes once these pastes are open to the air, as evaporation of water might change product properties rapidly or even may render the pastes unusable.

One of the pastes contains a polyacid as an important component of the glass ionomer composition. The polyacid has the capability to hold back water and prevent evaporation.

However, the paste which contains the acid-reactive glass (ionomer glass) usually contains no component, which has a similar capability.

Adding substances for that purpose is possible, but substances, which do not take part in the glass ionomer reaction, often negatively influence the mechanical properties, like strength, of the composition after hardening.

US 2003/0136303 A1 (Kobayashi et al.) describes a paste type dental glass ionomer cement composition comprising a first paste containing a polymer of an alpha-beta unsaturated carboxylic acid and water, and a second paste containing a fluoro aluminosilicate glass powder, water and a small amount of a thickening agent. As thickening agents carboxymethyl cellulose components are suggested. Compressive strength values in the range of 71 to 88 MPa are reported.

EP 3 100 712 A1 (GC) describes a filler for dental glass ionomer cements. In addition, paste/paste glass ionomer compositions are described containing glycerine as a further liquid component besides water.

EP 2 163 233 A1 (GC) describes a paste-type dental cement comprising a phosphoric acid and/or polymer of an alpha-beta unsaturated carboxylic acid, an oxide powder capable of reacting with said acid, water and a liquid which is not capable of reacting with the oxide powder. As possible liquids, polyhydric alcohols are suggested. The paste-type dental cement is for use as temporary cement and allows and easy removal of dental prostheses. Compressive strength values in the range of 8 to 31 MPa are reported.

WO 2017/015193 A1 (3M) relates to a kit of parts for producing a glass ionomer cement. The kit comprises a Paste A comprising water, acid-reactive inorganic filler C and non acid-reactive filler A and Paste B comprising water, polyacid, complexing agent and non acid-reactive filler B, wherein the mean particle size of non acid-reactive filler B is larger than the mean particle size of non acid-reactive filler A.

GB 2 021 123 A (3M) describes a surgical cement useful in dentistry, which is formed by mixing a) a concentrated non-gelling aqueous solution of polycarboxylic acid and b) an aqueous suspension of metal oxide or polyvalent-cation-containing glass powder. For retarding the tendency for the paste to dry out in storage the addition of sorbitol, glycerol or other humectants is suggested. In the examples the ratio of water to sorbitol is about 30:1.

SUMMARY

There is a need for a water-containing glass ionomer composition for dental use, which can be provided as a paste/paste system with sufficient storage stability.

Further, the composition obtained after mixing the two pastes should have good mechanical properties after hardening.

It would also be desirable to have a water containing paste/paste system available, which is less sensitive to dry out during storage and use.

If possible, an undesired water-loss or dry-out of the water-containing paste of the kit or parts during storage and use should be prevented.

On the one hand, an undesired water-loss or dry-out could make the mixing or the pastes more complicated.

On the other hand, an undesired water-loss or dry-out could result in an inadequate mixing ratio, which might have a negative impact on the physical properties and performance of the hardened composition.

One or more of the above objects are addressed by the invention described in the present text and claims.

In one embodiment, the invention features a kit or parts for preparing a glass ionomer composition for dental use as described in the present text and claims, the kit or parts comprising a Paste A and a Paste B, Paste A comprising
    water,
    acid-reactive inorganic filler A,
    non acid-reactive filler B1,
    sugar alcohol with 6 hydroxyl moieties, Paste B comprising
    water,
    polyacid,
    non acid-reactive filler B2,
    the ratio of sugar alcohol in parts by weight to water in Paste A being preferably in a range of 1:10 to 1:3,
    the sugar alcohol being present in an amount of not more than 2 wt. % and the water being present in an amount of not more than 15 wt. %, wt. % with respect to the whole composition obtained when mixing Paste A and Paste B.

The invention also relates to a process of producing a dental composition by mixing the respective pastes of the kit of parts as described in the present text and the claims.

Moreover, the invention relates to a hardened glass ionomer composition for dental use, the hardened composition being obtainable by mixing Paste A and Paste B of the kit of parts described in in the present text and letting the mixture harden, wherein the hardened glass ionomer composition is characterized by the following parameters alone or in combination: a) flexural strength: above 20 MPa and/or b) compressive strength: above 100 MPa.

Unless defined differently, for this description the following terms shall have the given meaning:

A "dental composition" or a "composition for dental use" or a "composition to be used in the dental field" is any composition which can be used in the dental field. In this respect, the composition should be not detrimental to the patients' health and thus free of hazardous and toxic components being able to migrate out of the composition. Dental compositions are typically hardenable compositions, which can be hardened at ambient conditions, including a temperature range from 15 to 50° C. or from 20 to 40° C. within a time frame of 30 min or 20 min or 10 min. Higher temperatures are not recommended as they might cause pain to the patient and may be detrimental to the patient's health. Dental compositions are typically provided to the practitioner in comparable small volumes, that is volumes in the range from 0.1 to 100 ml or from 0.5 to 50 ml or from 1 to 30 ml. Thus, the storage volume of useful packaging devices is within these ranges.

A "polymerizable component" is any component which can be cured or solidified e.g. by heating to cause polymerization or chemical crosslinking, or e.g. by radiation-induced polymerization or crosslinking, or e.g. using a redox initiator. A polymerizable component may contain only one, two, three or more polymerizable groups. Typical examples of polymerizable groups include unsaturated carbon groups, such as a vinyl group being present e.g. in a (methyl)acrylate group.

The dental composition described in the present text does not contain polymerizable components in an amount above 0.5 or above 1 wt. % with respect to the whole composition. The dental composition described in the present text is essentially free of polymerizable components or monomers bearing (meth)acrylate groups.

A "monomer" is a chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i. e., $CH_2=CH-C(O)-O-$) and/or a methacryloxy group (i. e., $CH_2=C(CH_3)-C(O)-O-$).

An "initiator" is a substance being able to start or initiate the curing process of polymerizable components or monomers, e.g. redox/auto-cure chemical reaction or by a radiation induced reaction or by a heat induced reaction.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "d50/µm" with regard to particle size measurement means that 50% of the particles in the analysed volume, the particles have a size below x µm. E.g., a particle size value of below 100 µm (d50) means that within the analysed volume, 50% of the particles have a size below 100 µm.

"Paste" shall mean a soft, viscous mass of solids dispersed in a liquid.

"Viscous" means a viscosity above 50 Pa*s (at 23° C.).

A "liquid" means any solvent or liquid being able to at least partially disperse or dissolve a component at ambient conditions (e.g. 23° C.). A liquid typically has a viscosity below 10 or below 8 or below 6 Pa*s.

"Glass ionomer cement" or "GIC" shall mean a cement curing or hardening by the reaction between an acid-reactive glass and a polyacid in the presence of water.

"Resin modified glass ionomer cement" or "RM-GIC" shall mean a GIC containing in addition polymerizable component(s), an initiator system and typically 2-hydroxyl-ethyl-methacrylate (HEMA).

"Acid-reactive filler" shall mean a filler that chemically reacts in the presence of a (poly)acid leading to a hardening reaction.

"Non acid-reactive filler": shall mean a filler, which does not show a chemical hardening reaction within about 30 min, if mixed with a (poly)acid at ambient conditions (e.g. 23° C.).

To distinguish an acid-reactive filler from a non acid-reactive filler the following test can or is to be conducted: A composition is prepared by mixing Part A with Part B in a mass ratio of 3 to 1, wherein: Part A contains: filler to be analysed: 100 wt. %; Part B contains: poly (acrylic acid co maleic acid) (Mw: about 20,000+/−3,000): 43.6 wt. %, water: 47.2 wt. %, tartaric acid: 9.1 wt. %, benzoic acid: 0.1 wt. %.

Examples of non acid-reactive fillers include quartz glass and cristobalite. Further examples are given in the text below.

"Cation reduced aluminosilicate glasses" shall mean a glass having a lower content of cations in the surface region of the glass particle compared with the inner region of the glass particle. These glasses react much slower upon contact with a solution of polyacrylic acid in water as compared to typical acid-reactive fillers. Cation reduction can be achieved by a surface treatment of the glass particles. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution.

"Polyacid" or "polyalkenoic acid" shall mean a polymer having a plurality of acidic repeating units (e.g. more than 10 or more than 20 or more than 50). That is, the acidic repeating units are attached to or pending from the backbone of the polymer.

"Complexing or chelating agent" shall mean a low molecular agent comprising moieties and being able to form a complex with metal ions like calcium or magnesium; e.g. tartaric acid.

A "storage stable composition" is a composition which can be stored for an adequate period of time (e.g. at least 12 months under ambient conditions) without showing significant performance issues (e.g. reduced flexural or compressive strength), and/or which does not harden over time and/or which does not separate over time.

A substance is characterized as "hygroscopic", if the substance is able to absorb moisture from air.

By "hardenable" or "curable" is meant that the composition can be cured or solidified, e.g. by conducting a glass ionomer cement reaction without the need for an additional curing system like chemical cross-linking, radiation-induced polymerization or crosslinking.

A composition is "essentially or substantially free of" a certain component, if the composition does not contain said component as an essential feature. Thus, said component is not willfully added to the composition either as such or in combination with other components or ingredient of other components.

A composition being essentially free of a certain component usually contains the component in an amount of less than 1 wt. % or less than 0.5 wt. % or less than 0.1 wt. % or less than 0.01 wt. % with respect to the whole composition or material. The composition may not contain the said component at all. However, sometimes the presence of a small amount of the said component is not avoidable e.g. due to impurities contained in the raw materials used.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

As used herein, "a", "an", "the", "at least one" and "one or more" are used interchangeably. The terms "comprise" or "contain" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.). The term "comprise" shall include also the terms "consist essentially of" and "consists of".

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

DETAILED DESCRIPTION

The use of a sugar alcohol helps to mitigate the problem of dry-out or water-loss of a glass-ionomer composition, which is provided in form of a paste/paste system, during use or storage.

An improved storage stability is desired, if the delivery device containing the paste is left open for a longer period of time, or when the paste is not immediately used, but left on a mixing block for a certain period of time. This may cause an undesired evaporation of the water contained in the paste.

Further, the composition obtained after mixing the pastes shows adequate physical properties, like sufficient compressive strength, after hardening. Thus, the use of a sugar alcohol does not negatively impact the mechanical properties of the hardened composition.

In addition, as the sugar alcohol has a sufficiently low molecular weight, the viscosity of the respective paste is not negatively affected.

Particularly, it was found that on the one hand the sugar alcohol has a sufficient water-binding capacity for preventing the dry-out of a water-containing paste, and on the other hand the use of the sugar alcohol does not negatively influence the physical properties of the hardened composition, particularly, if the additive is used in an adequate amount. The invention is directed to a kit of parts. The kit of parts described in the present text comprises two pastes, Paste A and Paste B.

Upon mixing those two pastes, a composition in the form of a further paste is obtained. That composition hardens by a so-called glass ionomer cement reaction.

Paste A contains water, acid-reactive filler A, non acid-reactive filler B1 and sugar alcohol.

Paste B contains water, polyacid, non acid-reactive filler B2.

Paste A can typically be characterized by the following features alone or in combination:
  a) viscosity: 100 to 50,000 Pa*s or 1,000 to 40,000 Pa*s at 23° C., measured at a shear rate of 20 $s^{-1}$;
  b) density: 1.5 to 3.0 $g/cm^3$;
  c) pH value: 5 to 10, e.g. if determined with a pH indicator for 1 g Paste A dispersed in 10 ml de-ionized water and stirred for 5 min.

The combination of the features a) and c) is sometimes preferred.

Paste A contains a sugar alcohol with 6 hydroxy moieties, preferably a sugar alcohol with 6 carbon atoms and 6 hydroxy moieties.

It has been found that this sugar alcohol is sufficiently hygroscopic to address the above object.

Further, the use of this sugar alcohol does not negatively influence physical properties like sufficient compressive strength to an undesirable extent.

Examples of sugar alcohols which can be used include mannitol, sorbitol, and mixtures thereof, with sorbitol being preferred.

The sugar alcohol is present in the composition obtained when combining Paste A and Paste B in an amount of not more than 2 wt. % or not more than 1.5 wt. %.

It can be preferred, if the ratio of sugar alcohol in parts by weight to acid-reactive inorganic filler A in parts by weight in Paste A is in the range of 1:10 to 1:100.

Alternatively, or in addition, it can be preferred, if the ratio of sugar alcohol in parts by weight to water in Paste A is in the range of 1:10 to 1:3.

Paste A contains an acid-reactive inorganic filler, designated as filler A.

The nature and structure of the acid-reactive filler A is not particularly limited unless the desired result cannot be achieved. The acid-reactive filler A has to be able to undergo a glass-ionomer cement reaction.

According to one embodiment, the acid-reactive filler A can be characterized by the following features alone or in combination:
a) Mean particle size: 1 to 25 μm;
b) (d10/μm): 0.5 μm to 3 μm; (d50/μm): 2 μm to 7 μm; (d90/μm): 6 μm to 30 μm;
c) pH value of a dispersion of 1 g filler stirred in 10 ml de-ionized water (having a pH of about 5) for 5 minutes: between 5 and 8.

The combination of features a) and b) or b) and c) can be preferred.

If the mean particle size of the acid-reactive filler A is above the range outlined above, the consistency of the composition obtained when mixing the compositions contained in the parts of the kit of parts described in the present text might not be adequate and the desired mechanical properties might be negatively affected.

If the mean particle size of the acid-reactive filler A is below the range outlined above, the setting time might be too fast.

Suitable acid-reactive fillers A include metal oxides, metal hydroxides, hydroxyapatite, acid-reactive glasses including aluminosilicate glasses and fluoro aluminosilicate glasses.

Typical metal oxides include barium oxide, strontium oxide, calcium oxide, magnesium oxide, zinc oxide.

Typical metal hydroxides include calcium hydroxide, magnesium hydroxide, strontium hydroxide and mixtures thereof.

Typical acid-reactive glasses include aluminosilicate glasses and in particular, fluoro-aluminasilicate ("FAS") glasses.

FAS glasses are particularly preferred. The FAS glass typically contains a sufficient amount of elutable cations so that a hardened dental composition can be obtained when the glass is mixed with the other components of the hardenable composition.

The FAS glass also typically contains a sufficient amount of elutable fluoride ions so that the hardened composition will have anticariogenic properties.

The glass can be made from a melt containing fluoride, silica, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Suitable FAS glasses are familiar to those skilled in the art, and are available from a wide variety of commercial sources, and many are found in currently available glass ionomer cements such as those commercially available under the trade designations Ketac™-Molar or Ketac™-Fil Plus (3M Oral Care), and FUJI™ IX (GC).

Fluoro aluminosilicate glasses can be prepared by fusing mixtures of silica, alumina, cryolite and fluorite.

Useful acid-reactive glasses can also be characterized by the Si/Al ratio. Fillers having a Si/Al ratio (by wt. %) of below 1.5 or 1.4 or 1.3 were found to be useful.

Suitable acid-reactive fillers are also commercially available from e.g. Schott AG (Germany) or Specialty Glass (US).

Mixtures of acid-reactive inorganic fillers A can be used, if desired.

The acid-reactive filler A is typically present in the following amount:
at least 45 or at least 50 or at least 55 wt. %;
utmost 95 or utmost 90 or utmost 85 wt. %;
range: 45 to 95 or 50 to 90 or 55 to 85 wt. %, wt. % with respect to the weight of Paste A.

If the amount of the acid-reactive filler is too high, mixing of the pastes of the kit of parts described in the present text might become more difficult. Furthermore, obtaining an adequate consistency and acceptable mechanical properties of the resulting composition might become difficult, as well.

If the amount of the acid-reactive filler is too low, formulating a suitable paste might become more difficult. Furthermore, the mechanical properties might become inferior.

Paste A contains a non acid-reactive filler, designated as filler B1.

A non acid-reactive filler is a filler, which either does not cure in a glass ionomer cement reaction at all, if combined with a polyacid in the presence of water, or only shows a delayed curing reaction.

A more precise definition of non acid-reactive filler is given above.

The nature and structure of the non acid-reactive filler B1 is not particularly limited, either unless the desired result cannot be achieved.

The non-acid reactive filler B1 is preferably an inorganic filler.

The non-acid reactive filler B1 should be non-toxic and suitable for use in the mouth of a human being.

The non-acid reactive filler B1 can be radiopaque or radiolucent.

According to one embodiment, the non acid-reactive filler B1 can be characterized by the following features alone or in combination:
a) Mean particle size: 10 nm to 500 nm; or from 10 to 200 nm
b) Containing no particles larger than 2 μm;
c) pH value of a dispersion of 1 g filler stirred in 10 ml de-ionized water for 5 minutes: between 7 and 11.

The combination of features a) and b) or b) and c) is sometimes preferred.

If the mean particle size of the non acid-reactive filler B1 is above the range outlined above, the consistency of the obtained paste might not be adequate and in addition it might become difficult to obtain the desired mechanical properties.

If the mean particle size of the non acid-reactive filler B1 is below the range outlined above, the desired consistency of the obtained paste might not be adequate.

Examples of suitable non acid-reactive fillers B1 are naturally occurring or synthetic materials including, but not limited to: kaolin; silica particles (e.g., submicron pyrogenic silicas such as those available under the trade designations "AEROSIL™", including "OX 50," "130," "150" and "200", silicas from Evonic, and HDK™, including "H15", "H20", "H2000" from Wacker, and CAB-O-SIL M5 silica from Cabot Corp.), alumina, titania and zirconia particles.

Mixtures of these non-acid-reactive fillers B1 are also contemplated.

Sometimes, the non acid-reactive filler B1 is provided as a dispersion or sol of particles in a liquid (e.g. water).

If the filler is provided as an aqueous dispersion or sol, the amount of water in the aqueous dispersion or sol has to be taken into account when the amount of water and filler in the composition is calculated or determined.

Suitable non acid-reactive fillers B1 are also commercially available as aqueous dispersions from e.g. Obermeier, Bad Berleburg, Germany under the trade name Levasil™, including type "50/50%", wherein the % value indicates the filler content in wt. %.

If desired, the surface of the particles of the non acid-reactive fillers B1 can be surface treated. Suitable surface-treating agents include silanes, e.g. trimethoxysilanes carrying an organic functional group to modify the chemical properties of the particles. Suitable silanes are e.g. silanes to modify the acidic properties (carrying amino groups or carrying carboxylic acid groups) or silanes to modify the hydrophobicity/hydrophilicity (carrying an alkane chain or carrying a polyethylene glycol chain).

According to one embodiment, the non acid-reactive filler B1 is selected from silica, (alumo)silicates, alumina and mixtures thereof.

The non acid-reactive filler B1 is typically present in the following amounts:
  at least 1 or at least 3 or at least 5 wt. %;
  utmost 50 or utmost 40 or utmost 30 wt. %;
  range: 1 to 50 or 3 to 40 or 5 to 30 wt. %.
wt. % with respect to the weight of Paste A.

Paste A also contains water.

The water can be distilled, de-ionized, or plain tap water. Typically, de-ionized water is used.

The amount of water should be sufficient to provide adequate handling and mixing properties and to permit the transport of ions, particularly in the cement reaction.

Water is typically present in the following amount:
  at least 5 or at least 6 or at least 7 wt. %;
  utmost 45 or utmost 30 or utmost 20 wt. %;
  range: 5 to 45 or 6 to 30 or 7 to 20 wt. %;
wt. % with respect to the weight of Paste A.

If the amount of the water is too low, obtaining a workable consistency of the obtained paste might become difficult.

If the amount of water is too high, obtaining a workable consistency of the obtained paste might become difficult, too. Furthermore, it will become difficult to achieve the desired mechanical properties and the paste might separate during storage.

Paste B can typically be characterized by the following features alone or in combination:
  a) viscosity: 100 to 50,000 Pa*s or 1,000 to 40,000 Pa*s at 23° C., measured at a shear rate of 20 $s^{-1}$;
  b) density: 1.5 to 3.0 $g/cm^3$;
  c) pH value: 1 to 4, e.g. if determined with a pH indicator for 1 g Paste A dispersed in 10 ml de-ionized water and stirred for 5 min.

The combination of the following features is sometime preferred: a) and b) or a) and c).

Paste B contains water, too. The water contained in Paste B is as described for Paste A.

Water is typically present in the following amount:
  at least 5 or at least 7 or at least 9 wt. %;
  utmost 60 or utmost 55 or utmost 50 wt. %;
  range: 5 to 60 or 7 to 55 or 9 to 50 wt. %;
wt. % with respect to the weight of Paste B.

Paste B contains a polyacid.

The nature and structure of the polyacid is not particularly limited, either, unless the desired result cannot be achieved.

However, the polyacid should have a molecular weight sufficient to provide good storage, handling, and mixing properties, as well as to yield good material properties in the glass ionomer material.

According to one embodiment, the polyacid can be characterized by the following features alone or in combination:
  being a solid (at 23° C.);
  molecular weight (Mw): 2,000 to 250,000 or 4,000 to 100,000 g/mol (evaluated against a polyacrylic acid sodium salt standard using gel permeation chromatography).

If the molecular weight of the polyacid is too high, obtaining a workable consistency of the obtained paste when mixing the compositions contained in the kit of parts described in the present text might become difficult. Furthermore, preparation of the compositions might become difficult, too. In addition, the obtained mixture or composition might become too sticky (i.e. adheres to the dental instrument used for application).

If the molecular weight of the polyacid is too low, the viscosity of the obtained paste might become too low and the mechanical properties inferior.

Typically, the polyacid is a polymer having a plurality of acidic repeating units.

The polyacid to be used for the cement composition described in the present text is substantially free of polymerizable groups.

The polyacid need not be entirely water soluble, but typically it is at least sufficiently water-miscible so that it does not undergo substantial sedimentation when combined with other aqueous components.

The polyacid is hardenable in the presence of, for example, an acid-reactive filler and water, but does not contain ethylenically unsaturated groups.

That is, the polyacid is a polymer obtained by polymerising an unsaturated acid. However, due to the production process, a polyacid might still contain unavoidable traces of free monomers (e.g. up to 1 or 0.5 or 0.3 wt. % with respect to the amount of monomers used).

Typically, the unsaturated acid is an oxyacid (i.e., an oxygen containing acid) of carbon, sulfur, phosphorous, or boron. More typically, it is an oxyacid of carbon.

Suitable polyacids include, for example, polyalkenoic acids such as homopolymers and copolymers of unsaturated mono-, di-, or tricarboxylic acids.

Polyalkenoic acids can be prepared by the homopolymerization and copolymerization of unsaturated aliphatic carboxylic acids, e.g., acrylic acid, methacrylic acid, itaconic acid, maleic acid, glutaconic acid, aconitic acid, citraconic acid, mesaconic acid, fumaric acid, and tiglic acid.

Suitable polyacids also include alternating copolymers of maleic acid and ethylene (e.g. in a molar one to one ratio).

Suitable polyacids are also described in the following documents: U.S. Pat. No. 4,209,434 (Wilson et al.), U.S. Pat. No. 4,360,605 (Schmitt et al.). The content of these documents with respect to the description of the polyacid is herewith incorporated by reference.

Suitable polyacids are also included as aqueous solutions in the liquid component of commercially available products from e.g. 3M Oral Care (e.g. Ketac™ Fil Plus Handmix) or GC (e.g. Fuji™ IX GP Handmix).

The amount of polyacid should be sufficient to react with the acid-reactive filler and to provide an ionomer composition with desirable hardening properties.

The polyacid is typically present in the following amount:
  at least 3 or at least 5 or at least 10 wt. %;
  utmost 80 or utmost 75 or utmost 70 wt. %;
  range: 3 to 80 or 5 to 75 or 10 to 70 wt. %.
wt. % with respect to the weight of Paste B.

If the amount of polyacid is too high, obtaining a workable consistency of the obtained paste when mixing the compositions contained in the kit of parts described in the present text might become difficult. Furthermore, preparation of the compositions might become difficult. In addition, the obtained mixture or composition might become too sticky (i.e. adheres to the dental instrument used for application).

If the amount of polyacid is too low, obtaining a workable consistency of the obtained paste when mixing the compositions contained in the kit of parts described in the present text might become difficult, either. Furthermore, it might become difficult to achieve the desired mechanical properties.

Paste B contains a non acid-reactive filler B2.

The non acid-reactive filler B2 contained in Paste B can be the same or a different material as the non acid-reactive filler B1 described for Paste A.

However, the mean particle size of the non acid-reactive filler B2 contained in Paste B is typically larger than the mean particle size of the non-acid reactive filler B1 contained in Paste A.

According to one embodiment, the non acid-reactive filler B2 can be characterized by at least one or more or all of the following parameters:
 a) Mean particle size: 1 to 10 μm;
 b) (d10/μm): 0.2 μm to 2 μm; (d50/μm): 0.5 μm to 5 μm; (d90/μm) 1 μm to 15 μm;
 c) pH value of a dispersion of 1 g filler stirred in 10 ml de-ionized water for 5 minutes: between 4 and 7 or 4 to 6.

The combination of features a) and c) or b) and c) is sometimes preferred.

Examples of suitable non acid-reactive fillers B are naturally occurring or synthetic materials including, but not limited to: quartz, cristobalite; nitrides (e.g., silicon nitride); glasses derived from, e.g., Zr, Sr, Ce, Sb, Sn, Ba, Zn, and Al; borosilicate glass; kaolin; silica particles (e.g. quartz glass or pyrogenic silica of suitable particle size), alumina, titania and zirconia particles.

According to one embodiment, the non acid-reactive filler B is selected from quartz, titanium oxide, silica, alumina, aluminosilicates and mixtures thereof.

If desired, the surface of the particles of the acid-reactive filler B2 can be surface treated. Suitable surface-treating agents include silanes, e.g. trimethoxysilanes carrying an organic functional group to modify the chemical properties of the particles. Suitable silanes are e.g. silanes to modify the acidic properties (carrying amino groups or carrying carboxylic acid groups) or silanes to modify the hydrophobicity/hydrophilicity (carrying an alkane chain or carrying a polyethylene glycol chain).

Examples of suitable non acid-reactive fillers B2 are naturally occurring or synthetic materials including, but not limited to: silica (e.g., submicron pyrogenic silicas such as those available under the trade designations "AEROSIL™", including "OX 50," "130," "150" and "200", silicas from Evonic, and HDK™, including "H15", "H20", "H2000" from Wacker and CAB-O-SIL™ M5 silica from Cabot Corp.), quartz, cristobalite (e.g Sikron™ SF 6000), borosilicate glass, alumina, titania and zirconia particles and mixtures thereof.

The non acid-reactive filler B2 is typically present in the following amounts:
 at least 2 or at least 5 or at least 7 wt. %;
 utmost 90 or utmost 80 or utmost 75 wt. %;
 range: 2 to 90 or 5 to 80 or 7 to 75 wt. %;
wt. % with respect to the weight of Paste B.

Paste B may contain a complexing agent or chelating agent. The terms complexing or chelating agent are used interchangeable.

The nature and structure of the complexing or chelating agent is not particularly limited, either unless the desired result cannot be achieved.

The complexing agent is typically used for adjusting the curing properties of the hardenable composition, particularly for adjusting the working time.

The complexing agent can be characterized by the following features alone or in combination:
 solubility: soluble in water (at least 50 g/l water at 23° C.);
 molecular weight: from 50 to 500 g/mol, or from 75 to 300 g/mol.

Specific examples of the complexing agent include tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof.

Further examples can be found e.g. in U.S. Pat. No. 4,569,954 (Wilson et al.). The content of this document is herewith incorporated by reference.

The complexing agent is typically added to that paste containing the polyacid only, i.e., to Paste B.

If present, the complexing agent is typically present in the following amount:
 at least 0.1 or at least 1.0 or at least 1.5 wt. %;
 utmost 15 or utmost 12 or utmost 10 wt. %;
 range: 0.1 to 15 or 1.0 to 12 or 1.5 to 10 wt. %;
wt. % with respect to the weight of the Paste B.

Either Paste A or Paste B can also contain solvent(s).

Adding solvent(s) or co-solvent(s) may help to adjust the viscosity and consistency of the composition.

Examples of solvent(s) which can be used include alcohols (e.g. methanol, ethanol, propanol), polyalcohols/polyols (e.g. polyethylene glycol, ethylene glycol, glycerol) and mixtures thereof.

Either Paste A or Paste B or Paste A and Paste B can also contain additive(s).

Additives which might be present include indicator(s), dye(s), pigment(s), surfactant(s), buffering agent(s), stabilizer(s), preservative agent(s) (e.g., benzoic acid).

Combination of any of the above additives may also be employed. The selection and amount of any one such additive can be selected by one skilled in the art to accomplish the desired result without undue experimentation.

There is no need for those component(s) to be present, however, if present, the individual component is typically present in an amount of less than 5 wt. % or less than 3 wt. % or less than 1 wt. % with respect to the weight of the respective Paste (A or B).

Useful ranges of those component(s) include 0.01 to 5 wt. % or 0.05 to 3 wt. % or 0.05 to 1 wt. %, wt. % with respect to the weight of the respective Paste A or B.

The cement composition obtained or obtainable by mixing the two pastes of the kit of parts described in the present text fulfils at least one or both of the following parameters before or during hardening:
 setting time: within 10 or 8 or 6 min;
 working time: within 7 or 5 or 3 min.

If desired, the hardening behaviour can be determined as described in more detail in the example section below.

The cement composition described in the present text typically has a sufficient working time allowing the practitioner not only to adequately mix the composition but also to apply the composition to the surface of a crown, bridge, root canal or prepared tooth.

Furthermore, the cement composition described in the present text has an adequate setting time, which is time saving for the practitioner and convenient for the patient.

The glass ionomer composition obtained when combining Paste A and Paste B of the kit of parts described in the present text comprises:
- acid-reactive inorganic filler(s) A in an amount of 20 to 60 wt. %,
- non acid-reactive filler(s) B1 in an amount of 1 to 20 wt. %,
- non-acid-reactive filler(s) B2 in an amount of 1 to 40 wt. %,
- polyacid(s) in an amount of 1 to 45 wt. %,
- water in an amount of 5 to 15 wt. %,
- sugar alcohol(s) in an amount of 0.1 to 2 wt. %,
- additive(s) in an amount of 0 to 5 wt. %, wt. % with respect to the amount of the whole composition.

The amount of fillers (fillers A, B1 and B2) contained in the composition obtained when mixing Paste A and Paste B is typically above 50 or above 55 or above 60 wt. %.

A high filler content combined with a low water content may help to improve mechanical properties of the hardened composition, like compressive strength.

The water content of the composition obtained when mixing Paste A and Paste B is typically not more than 15 or not more than 12 wt. % or not more than 10 wt. %.

A low water content typically may help to improve physical properties like compressive strength, as well.

The pastes of the kit of part described in the present text can be produced by simply mixing the individual components of the respective pastes.

If needed, the filler particles can be milled to the desired particle size using equipment known to the skilled person like ball mills.

Mixing can be accomplished either by hand or with a mechanical device like a mixer or kneading machine. The mixing duration can vary depending on the composition and the mixing device and should be sufficiently long to obtain a homogeneous paste.

During storage, the pastes described in the present text are typically packaged in a suitable packaging device.

The pastes may be contained in separate sealable vessels (e.g., made out of plastic, glass or metal).

For use, the practitioner may take adequate portions of the pasty components from the vessels and mix the portions by hand on a mixing pad.

In an alternative embodiment, the pastes are contained in separate compartments of a storing device.

The storing device typically comprises two compartments for storing the respective pastes, each compartment being equipped with a nozzle for delivering the respective paste. Once delivered in adequate portions, the pastes can then be mixed by hand on a mixing pad.

According to another preferred embodiment, the storing device has an interface for receiving a static mixing tip. The mixing tip is used for mixing the respective pastes. Static mixing tips are commercially available e.g. from Sulzer-Mixpac company.

Suitable storing devices include cartridges, syringes and tubes.

The storing device typically comprises two housings or compartments having a front end with a nozzle and a rear end and at least one piston movable in the housing or compartment.

Cartridges which can be used are described e.g. in US 2007/0090079 (Keller) or U.S. Pat. No. 5,918,772 (Keller et al.), the disclosure of which is incorporated by reference. Some of the cartridges which can be used are commercially available e.g. from SulzerMixpac AG (Switzerland). Static mixing tips which can be used are described e.g. in US 2006/0187752 (Keller) or in U.S. Pat. No. 5,944,419 (Streiff), the disclosure of which is incorporated by reference. Mixing tips which can be used are commercially available from SulzerMixpac AG (Switzerland), as well.

Other suitable storing devices are described e.g. in WO 2010/123800 (Boehm et al.), WO 2005/016783 (Reidt et al.), WO 2007/104037 (Broyles et al.), WO 2009/061884 (Boehm et al.), in particular the device shown in FIG. 14. The content of these references is herewith incorporated by reference, as well.

Alternatively, paste/paste compositions described in the present text can be provided in two individual syringes and the individual pastes can be mixed by hand prior to use.

Thus, the invention is also directed to a device for storing the kit of parts described in the present text, the device comprising two compartments, Compartment A and Compartment B, Compartment A containing Paste A and Compartment B containing Paste B, Paste A and Paste B being as described in the present text, Compartment A and Compartment B both comprising a nozzle or an interface for receiving an entrance orifice of a static mixing tip.

The mixing ratio of Paste A and Paste B is typically in the range of 2:1 to 1:2 with respect to volume, preferably 1:1.

Alternatively, the mixing ratio of Paste A and Paste B is typically 3:1 to 1:1 with respect to weight, preferably in the range of 2:1 to 1:1.

The invention is also directed to the hardened composition obtainable or obtained by mixing Paste A and Paste B of the kit of parts described in the present text.

The glass ionomer composition obtained or obtainable by mixing the two pastes of the kit of parts described in the present text fulfils the following features alone or in combination after hardening:
- Flexural strength: above 20 or above 25 MPa or within in a range of 20 to 50 MPa or 25 MPa to 50 MPa, determined according to EN-ISO 9917-2:2010 with the proviso that for covering the composition a glass slab is used instead of a foil;
- Compressive strength: above 100 or above 120 or above 150 MPa or above 160 MPa or within in a range of 100 to 250 MPa or 150 MPa to 250 MPa, determined according to EN-ISO 9917-1:2007 with the proviso that for covering the composition a glass slab is used instead of a foil.

If desired, these parameters can be determined as described in the example section below.

Compared to state of the art glass ionomer cements available on the market, the cement composition described in the present text can easily be mixed and has adequate mechanical properties like compressive strength without affecting other important parameters like setting time.

The composition obtained or obtainable when mixing the respective pastes described in the present text is particularly useful as or for producing a dental cement, dental filling material, dental core build-up material or as dental root channel filling material.

A typical application comprises the following steps:
a) mixing Paste A and Paste B to obtain a hardenable composition,
b) applying the hardenable composition to the surface of hard dental tissue,
c) letting the hardening composition harden.

The kit of parts may also contain in addition mixing equipment, including a mixing pad and/or a mixing spatula.

The kit of parts described in the present text typically also contains an instruction for use.

The instruction for use typically contains hints how to store the kit of parts, mix the pastes of the kit of parts and/or how to apply the composition obtained by mixing the pastes to the surface of hard dental tissue.

Further preferred embodiments are described below:

Embodiment 1

A kit of parts comprising Paste A and Paste B being characterized as follows:
Paste A comprising
water in an amount of 5 to 20 wt. %,
acid-reactive inorganic filler A
in an amount of 40 to 90 wt. %,
being selected from metal oxides, metal hydroxides, hydroxyapatite, fluoroaluminosilicate glasses and mixtures thereof,
non acid-reactive filler B1,
in an amount of 5 to 20 wt. %,
being selected from silica particles,
sugar alcohol
in an amount of 0.5 to 2.0 wt. %
wt. % with respect to the weight of Paste A,
Paste B comprising
water in an amount of 9 to 20 wt. %,
polyacid in an amount of 10 to 70 wt. %,
chelating agent in an amount of 0.1 to 12 wt. %,
non acid-reactive filler B2
in an amount of 5 to 70 wt. %,
being selected from quartz, silica, alumina, titania, zirconia and mixtures thereof,
wt. % with respect to the weight of Paste B.

Embodiment 2

A kit of parts comprising Paste A and Paste B being characterized as follows:
Paste A comprising
water in an amount of 7 to 15 wt. %,
acid-reactive inorganic filler A
in an amount of 60 to 90 wt. %,
the acid-reactive inorganic filler A having a mean particle size in the range of 1 to 15 μm and
being selected from metal oxides, metal hydroxides, hydroxyapatite, fluoroaluminosilicate glasses and mixtures thereof,
non acid-reactive filler B1,
in an amount of 5 to 20 wt. %,
being selected from silica particles having a mean particle size in the range of 10 to 500 nm,
sugar alcohol
in an amount of 0.5 to 1.5 wt. % and
being sorbitol,
wt. % with respect to the weight of Paste A,
Paste B comprising
water in an amount of 10 to 20 wt. %,
polyacid in an amount of 10 to 70 wt. %,
chelating agent in an amount of 0.1 to 10 wt. %,
non acid-reactive filler B2
in an amount of 5 to 70 wt. %,
being selected from quartz, silica, alumina, titania, zirconia and mixtures thereof,
wt. % with respect to the weight of Paste B.

Embodiment 3

A kit of parts comprising Paste A and Paste B being characterized as follows:
Paste A comprising
water in an amount of 6 to 15 wt. %,
acid-reactive inorganic filler A
in an amount of 40 to 90 wt. %,
the acid-reactive inorganic filler A having a mean particle size in the range of 1 to 15 μm and
being selected from metal oxides, metal hydroxides, hydroxyapatite, fluoroaluminosilicate glasses and mixtures thereof,
non acid-reactive filler B1,
in an amount of 5 to 15 wt. %,
being selected from silica particles having a mean particle size in the range of 10 to 500 nm
sugar alcohol
in an amount from 0.5 to 2.0 wt. % and
being sorbitol,
wt. % with respect to the weight of Paste A,
Paste B comprising
water in an amount of 10 to 20 wt. %,
polyacid in an amount of 10 to 70 wt. %,
chelating agent in an amount of 0.1 to 10 wt. %,
non acid-reactive filler B2
in an amount of 5 to 70 wt. %,
being selected from quartz, silica, alumina, titania, zirconia and mixtures thereof,
wt. % with respect to the weight of Paste B,
neither Paste A nor Paste B comprising polymerizable component(s) in an amount above 1 wt. % with respect to the weight of the composition obtained when mixing Paste A and Paste B,
Paste A and Paste B being provided in a ratio of 2:1 to 1:2 with respect to volume.

The respective components described in the embodiments correspond to the components described in the present text above.

The respective components described in the embodiments correspond to the components described in the present text above.

Typically, neither Paste A nor Paste B or nor Paste A and Paste B of the kit of parts described in the present text do contain either of the following components alone or in combination:
a) hydroxyl ethyl methacrylate (HEMA) in an amount above 1 wt. % or above 0.5 wt. %; b) polymerizable component(s) in an amount above 1 wt. % or above 0.5 wt. %;
c) initiator component(s) suitable to cure polymerizable component(s) or monomer(s) in an amount above 1 wt. % or above 0.5 wt. %;
d) inhibitor(s) like methoxyphenol or 3,5-Di-tert-butyl-4-hydroxytoluol in an amount above 1 wt. % or above 0.5 wt. %;
e) desiccant(s) like zeolithe(s) in an amount above 1 wt. % or above 0.5 wt. %; wt. % with respect to the weight of Paste A or Paste B.

Thus, the composition obtained when mixing the powder and liquid part of the kit of parts described in the present text is not a so-called resin-modified glass ionomer cement (RM-GIC) and thus does not contain a curing system based on polymerization.

In particular, the cement composition described in the present text does not contain a redox-initiator system or a thermally induced initiator system or a radiation induced initiator system.

In particular, the cement composition described in the present text does not contain the following components (a) and (b),
(b) and (c),
(a), (b) and (c),
(b), (c) and (d), or
(a), (b), (c) and (d)

in an amount above 1 wt. % or above 0.5 wt. % or above 0.1 wt. % with respect to each component and with respect to the weight of the whole composition.

That is, the cement composition described in the present text is typically essentially free of either of these components alone or in combination.

All components used in the dental composition of the invention should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Particle Size (Suitable for Micro-Sized Particles)

The particle size distribution including the mean particle size was determined with a Cilas 1064 (FA. Quantacrome) particle size detection device. During the measurement, ultrasonic was used to accurately disperse the sample.

Particle Size (Suitable for Nano-Sized Particles)

Particle size measurements were made using a light scattering particle sizer equipped with a red laser having a 633 nm wavelength of light (obtained under the trade designation "ZETA SIZER—Nano Series, Model ZEN3600" from Malvern Instruments Inc., Westborough, MA). Each sample was analyzed in a one-centimeter square polystyrene sample cuvette. The sample was diluted 1:100, e.g. 1 g of sample was given to 100 g of de-ionized water and mixed. The sample cuvette was filled with about 1 gram of diluted sample. The sample cuvette was then placed in the instrument and equilibrated at 25° C. The instrument parameters were set as follows: dispersant refractive index 1.330, dispersant viscosity 0.8872 mPa*s, material refractive index 1.43, and material absorption value 0.00 units. The automatic size-measurement procedure was then run. The instrument automatically adjusted the laser-beam position and attenuator setting to obtain the best measurement of particle size.

The light scattering particle-sizer illuminated the sample with a laser and analyzed the intensity fluctuations of the light scattered from the particles at an angle of 173 degrees. The method of Photon Correlation Spectroscopy (PCS) was used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

In the scope of this document the Z-average size is referred to as "mean particle size".

Molecular Weight

If desired, the molecular weight (Mw) can be determined by gel permeation chromatography (GPC) against a polyacrylic acid sodium salt standard. In particular, the following equipment was found to be useful: PSS SECurity GPC System equipped with 2*PSS Suprema 3000A, 8*300 mm, 10 µm columns; eluent: 84 mM $Na_2HPO_4$+200 ppm $NaN_3$; flux rate: 1 ml/min.

Viscosity of Mixed Paste

If desired, the viscosity of the mixed pastes can be determined using a Physica MCR 301 Rheometer (Anton Paar, Graz, Austria) with a plate/plate geometry (PP15) at a constant shear rate of 1 $s^{-1}$ in rotation at 28° C.

The diameter of the plates is 10 mm and the gap between the plates is set to 2.0 mm. After hand mixing of both pastes in a 1:1 weight ratio for 20 s, the mixture (~160 mg) is placed on the plate. The viscosity measurement is started 1 min after the start of the hand mixing. One data point is recorded per second. The measuring time is 60 s and the viscosity is determined by averaging the 5 data points after 30 seconds of measurement.

Viscosity of Individual Paste A and B

If desired, the viscosity of Paste A and B can be measured using a Physica MCR 301 Rheometer (Anton Paar, Graz, Austria) with a plate/plate geometry (PP15) at a constant shear rate of 1 $s^{-1}$ in rotation at 28° C.

The diameter of the plates is 10 mm and the gap between the plates is set to 2.0 mm. Paste A or B (~160 mg) is placed on the plate. One data point is recorded per second. The measuring time is 60 s and the viscosity is determined by averaging the 5 data points after 30 seconds of measurement.

Compressive Strength (CS)

If desired, the compressive strength is determined according to the EN-ISO 9917-1:2007 with the proviso that for covering the composition a glass slab is used instead of a foil.

Cylindrical specimens with a diameter of 4 mm and a height of 6 mm are used. Specimens of the materials are prepared at room temperature and 50% relative humidity using split moulds. The moulds are placed on microscope slides and thoroughly filled with the mixed material to avoid incorporation of air bubbles. The filled moulds are immediately covered with another glass slab and fixed in a screw clamp with slight pressure to extrude excess material. The whole assembly is stored in water at 36° C. 1 h after start of mixing the specimens are removed from the moulds and immediately placed in water at 36° C. 6 specimens are prepared for each material. Materials are measured 24 h after start of mixing. The exact diameter of each specimen is measured prior to the measurement. The strength of the specimen IS measured by applying a compressive load using a Zwick universal testing machine (Zwick GmbH & Co. KG, Ulm, Germany) operating at a crosshead speed of 1 mm/min.

Compressive Strength Decrease (CS-D)

The compressive strength decrease of a sample can be determined by division of its CS value by the CS value of a comparative sample. Multiplication with 100% yields the CS-D value in percent.

Flexural Strength (FS)

If desired, flexural strength can be determined based on EN ISO 9917-2:2010 with the proviso that for covering the composition a glass slab is used instead of a foil.

The specimens are prepared as described for the compressive strength test above, except that rectangular-shaped split moulds with dimensions 25 mm×2 mm×2 mm are used to prepare the samples. The specimens are subjected to a 3-point bend on supports 20 mm apart at a crosshead speed of 1 mm/min.

Dry out Time (DOT)

150 mg of the composition to be analysed are put on a mixing block and moulded into a drop-like shape.

The composition was deformed a bit every minute with a probe to check the consistency of the paste.

When the paste drop cracked during deformation, it was defined as being "dried out" and the time taken as "dry out time".

Dry out Time Increase (DOT-I)

The Dry out Time Increase of a sample can be determined by division of its DOT value by the DOT value of a comparative sample and subtracting 1. Multiplication with 100% yields the DOT-I value in percent.

Storage Stability

If desired, storage stability can be determined according to the following process: The pastes are stored for a given period of time under the following conditions: about 50% relative humidity at 23° C. After storage, the composition obtained when mixing the pastes are analysed for mechanical performance. If the mechanical properties (e.g. flexural strength, compressive strength) do not deviate by more than +/−20%, the composition is considered storage stable.

Working Time

If desired, working time can be determined using a Physica MCR 301 Rheometer (Anton Paar, Graz, Austria) with a plate/plate geometry (PP08) at a constant shear rate in oscillation at 28° C.

The diameter of the plates is 8 mm and the gap between the plates is set to 0.75 mm. The pastes are hand mixed in a 1:1 weight ratio. About 200 mg of the mixture is then placed on the cylindrical platform. Tan δ is measured in dependency on the time in an oscillating measurement (frequency 1.25 Hz; deformation 1.75%). Afterwards, the working time is calculated using a customized algorithm.

Density

If desired, the density of the pastes can be measured by filling the pastes into a container of defined volume and by weighing the container with and without paste. The weight difference divided by the defined volume yields the density of the paste.

Materials

TABLE 1

| Name | Description | Availability | |
|---|---|---|---|
| Levasil ™ 50/50 treated with glymo silane | Non acid-reactive filler B1; dispersion of silica particles in water at about 50 wt. %; mean particle size of silica particles: 114 nm | Obermeier | N-SI |
| Aerosil ™ OX50 | Non acid-reactive filler B1; fumed silica | Evonic | HA (reference) |
| Amosil ™ FW 600 | Non acid-reactive filler B2; amorphous silica powder | Quarzwerke | P-SI |
| FAS glass | Acid-reactive filler A; mean particle size: 3.28 μm | 3M Oral Care | I-GL |
| Ketac ™ Fil Plus | Acid-reactive filler A; Powder component of Ketac ™ Fil Plus; mean particle size: 11.01 μm | 3M Oral Care | I-GL |
| Lithium chloride | Hygroscopic agent | Acros | HA |
| Calcium chloride | Hygroscopic agent | Acros | HA |
| Glycerol | Hygroscopic agent | Aldrich | HA |
| Sorbitol | Hygroscopic agent | Merck | HA |
| Tartaric acid | Complexing agent | Brenntag | TA |
| Polyacid | Acrylic acid/maleic acid co-polymer (1:1 co-polymer; Mw = 20,000 g/mol) | 3M Oral Care | PAZ |
| Benzoic acid | preservation agent | Aldrich | BA |

The following compositions were prepared:
Polyacid Paste Composition (Paste B)
A Polyacid Paste Composition (PAC) containing
  2.16 g de-ionized water,
  0.68 g tartaric acid and
  4.36 g polyacid,
  12.78 g amorphous silica powder and
  0.02 g benzoic acid
was prepared.
A homogeneous mixture was obtained by mixing the components in a kneading machine for 6 hours.

Ionomer Glass Paste Composition (Paste A)
An Ionomer Glass Composition (IGC) containing
  1.44 g surface-treated silica dispersion (Levasil™ 50/50 with glymo silane),
  0.85 g acid reactive filler A (FAS glass),
  7.60 g acid reactive filler A (Ketac™ Fil Plus),
  0.01 g benzoic acid
was prepared.
To this Ionomer Glass Paste Composition, the following components were added:
  IGC-RE1: 0.10 g fumed silica (Aerosil™ OX50)
  IGC-CE1: 0.10 g glycerol
  IGC-CE2: 0.20 g glycerol
  IGC-CE3: 0.10 g lithium chloride
  IGC-CE4: 0.20 g lithium chloride
  IGC-CE5: 0.10 g calcium chloride
  IGC-CE6: 0.20 g calcium chloride
  IGC-CE7: 0.023 g sorbitol
  IGC-IE1 0.10 g sorbitol
  IGC-IE2: 0.20 g sorbitol
A homogeneous mixture was obtained by mixing with a speed mixer 3× for 10 seconds, waiting for at least 24 hours and mixing again 1× for 10 seconds.
The respective Ionomer Glass Paste Compositions were tested with respect to the "Dry-out-Time". The results are given in Table 2 (cont.).
In addition, glass ionomer cement compositions were prepared by mixing Paste B (PAC) with the respective Paste A (Ionomer Glass Paste Compositions; IGC) at a ratio of 1:1.43 by weight with a spatula.
  Reference Example 1 (RE1): PAC mixed with IGC-RE1
  Comparative Example 1 (CE1): PAC mixed with IGC-CE1
  Comparative Example 2 (CE2): PAC mixed with IGC-CE2
  Comparative Example 3 (CE3): PAC mixed with IGC-CE3
  Comparative Example 4 (CE4): PAC mixed with IGC-CE4
  Comparative Example 5 (CE5): PAC mixed with IGC-CE5
  Comparative Example 6 (CE6): PAC mixed with IGC-CE6
  Comparative Example 7 (CE7): PAC mixed with IGC-CE7
  Inventive Example 1 (IE1): PAC mixed with IGC-IE1
  Inventive Example 2 (IE2): PAC mixed with IGC-IE2

The respective mixtures were filled into moulds and allowed to cure for 24 hours. The compressive strength was measured. The results are given in Table 2 (cont.).
In Table 2, the glass ionomer cement compositions are also described with respect to the content of the respective components in wt. %.

TABLE 2

|  | Water wt. % | HA wt. % | PA wt. % | N-SI wt. % | P-SI wt. % | I-GL wt. % | TA wt. % | BA wt. % | Water:HA in IGC paste |
|---|---|---|---|---|---|---|---|---|---|
| RE1 | 8.7 | 0.6 | 9.0 | 4.2 | 26.3 | 49.7 | 1.4 | 0.1 | 7.2:1 |
| CE1 | 8.7 | 0.6 | 9.0 | 4.2 | 26.3 | 49.7 | 1.4 | 0.1 | 7.2:1 |
| CE2 | 8.6 | 1.2 | 9.0 | 4.2 | 26.3 | 49.2 | 1.4 | 0.1 | 3.6:1 |
| CE3 | 8.7 | 0.6 | 9.0 | 4.2 | 26.3 | 49.7 | 1.4 | 0.1 | 7.2:1 |
| CE4 | 8.6 | 1.2 | 9.0 | 4.2 | 26.3 | 49.2 | 1.4 | 0.1 | 3.6:1 |
| CE5 | 8.7 | 0.6 | 9.0 | 4.2 | 26.3 | 49.7 | 1.4 | 0.1 | 7.2:1 |
| CE6 | 8.6 | 1.2 | 9.0 | 4.2 | 26.3 | 49.2 | 1.4 | 0.1 | 3.6:1 |
| CE7* | 8.7 | 0.1 | 9.0 | 4.2 | 26.3 | 50.2 | 1.4 | 0.1 | 31.3:1 |
| IE1 | 8.7 | 0.6 | 9.0 | 4.2 | 26.3 | 49.7 | 1.4 | 0.1 | 7.2:1 |
| IE2 | 8.6 | 1.2 | 9.0 | 4.2 | 26.3 | 49.2 | 1.4 | 0.1 | 3.6:1 |

*The ratio of Water:HA is in the range described in GB 2 021 123 A

TABLE 2

|  | CS [MPa] | CS-D [%] | DOT [min] | DOT-I [%] | Efficiency* |
|---|---|---|---|---|---|
| RE1 | 219 | 0 | 3 | 0.0 | n.d. |
| CE1 | 190 | 13 | 7 | 133.3 | 10.0 |
| CE2 | 154 | 30 | 15 | 400.0 | 13.5 |
| CE3 | 140 | 36 | 10 | 233.3 | 6.5 |
| CE4 | 130 | 41 | 18 | 500.0 | 12.3 |
| CE5 | 156 | 29 | 4 | 33.3 | 1.2 |
| CE6 | 128 | 42 | 5 | 66.7 | 1.6 |
| CE7 | 211 | 4 | 3 | 0.0 | 0.0 |
| IE1 | 214 | 2 | 7 | 133.3 | 61.0 |
| IE2 | 193 | 12 | 10 | 233.3 | 19.9 |

*= Quotient of DOT-I and CS-D;
n.d. = not defined;

Observation
  RE1: Fumed silica, an inorganic water-insoluble solid as neutral additive, has no significant capability to bind water, but the compressive strength of the corresponding reference example is high.
  CE1; CE2: Glycerol is an organic liquid and is sometimes used as an additive for GI pastes. It has a good ability to bind water, but its use caused a decrease in compressive strength.
  CE3; CE4: Lithium chloride is a hygroscopic inorganic salt with a good ability to bind water. However, its addition caused negative impact on compressive strength.
  CE5; CE6: Calcium chloride is a hygroscopic inorganic salt but compared to lithium chloride offers only little water binding capability. However, like LiCl, its use caused a decrease in compressive strength.
  CE7: Sorbitol is used, but in a lower amount compared to the Inventive Examples. The amount used is in the range suggested in GB 2 021 123 A. The ability to bind water is too small to be determined.

IE1; 1E2: Sorbitol is an organic solid. Its ability to bind water is similar to glycerol, but the decrease of compressive strength is lower.

The high efficiency of the used sugar alcohol to prevent the dry-out (DOT-I) on the one hand, and to not negatively affect compressive strength (CS-D) on the other hand becomes apparent, if the quotient of DOT-I and CS-D is calculated. High values are preferred, since they indicate an increase in dry-out-time with a low decrease of compressive strength.

What is claimed is:

1. A kit of parts for preparing a glass ionomer composition for dental use, the kit comprising a Paste A and a Paste B,
   Paste A comprising:
   water,
   acid-reactive inorganic filler A,
   non acid-reactive filler B1,
   sugar alcohol with 6 hydroxyl moieties,
   Paste B comprising:
   water,
   polyacid,
   non acid-reactive filler B2,
   the ratio of sugar alcohol to water in Paste A being in a range of 1:10 to 1:3 in parts by weight,
   the sugar alcohol being present in an amount of not more than 2 wt. % with respect to a whole composition obtained when mixing Paste A and Paste B and
   the water being present in an amount of not more than 15 wt. % with respect to the whole composition,
   wherein a hardened composition obtained by mixing Paste A and Paste B and letting the mixture harden is characterized by the following parameters alone or in combination:
   flexural strength: above 20 MPa determined according to EN-ISO 9917-2:2010 with the proviso that for covering the composition a glass slab is used instead of a foil;
   compressive strength: above 100 MPa determined according to EN-ISO 9917-1:2007 with the proviso that for covering the composition a glass slab is used instead of a foil.

2. The kit of parts according to claim 1, the sugar alcohol being selected from mannitol, sorbitol, and mixtures thereof.

3. The kit of parts according to claim 1, the ratio of sugar alcohol in parts by weight to acid-reactive inorganic filler A in parts by weight in Paste A being from 1:10 to 1:100.

4. The kit of parts according to claim 1, Paste A and Paste B being provided in a ratio of 2:1 to 1:2 with respect to volume.

5. The kit of parts according to claim 1 being characterized as follows:
   Paste A comprising:
   water in an amount of 5 to 20 wt. %,
   acid-reactive inorganic filler A in an amount of 40 to 90 wt. %,
   non acid-reactive filler B1 in an amount of 1 to 20 wt. %,
   sugar alcohol in an amount of 0.5 to 2.0 wt. %,
   wt. % with respect to the weight of Paste A,
   Paste B comprising:
   water in an amount of 9 to 20 wt. %,
   polyacid in an amount of 10 to 70 wt. %,
   non-acid reactive filler B2 in an amount of 5 to 70 wt. %,
   wt. % with respect to the weight of Paste B.

6. The kit of parts according to claim 1,
   the non acid-reactive filler B1 being selected from powders and powder dispersions, the particles of which have a mean particle size in the range of 10 nm to 500 nm,
   the non acid-reactive filler B2 being selected from powders, the particles of which have a mean particle size in the range of 1 to 10 μm.

7. The kit of parts according to claim 1, either Paste A or Paste B or Paste A and Paste B comprising in addition the following components alone or in combination:
   preservative agent(s);
   coloring agent(s);
   chelating agent(s);
   solvent(s).

8. The kit of parts according to claim 1,
   Paste A being characterized by the following parameters alone or in combination:
   viscosity: 100 to 50,000 Pa*s at 28° C., measured at a shear rate of 1 $s^{-1}$;
   pH value: 5 to 10;
   Paste B being characterized by the following parameters alone or in combination:
   viscosity: 100 to 50,000 Pa*s at 28° C., measured at a shear rate of 1 $s^{-1}$;
   pH value: 1 to 4.

9. The kit of parts according to claim 1 being characterized as follows:
   Paste A comprising:
   water in an amount of 6 to 20 wt. %,
   the acid-reactive inorganic filler A
      in an amount of 50 to 90 wt. %,
      the acid-reactive inorganic filler A having a mean particle size in the range of 1 to 15 μm and
      being selected from metal oxides, metal hydroxides, hydroxyapatite, fluoroaluminosilicate glasses and mixtures thereof,
   the non acid-reactive filler B1,
      in an amount of 5 to 15 wt. %
      being selected from silica particles having a mean particle size in the range of 10 to 500 nm
   the sugar alcohol
      in an amount of 0.5 to 2.0 wt. % and
      being sorbitol,
   wt. % with respect to the weight of Paste A,
   Paste B comprising:
   water in an amount of 10 to 20 wt. %,
   the polyacid in an amount of 10 to 70 wt. %,
   a chelating agent in an amount of 0.1 to 12 wt. %,
   the non acid-reactive filler B2
      in an amount of 5 to 70 wt. %,
      being selected from quartz, silica, alumina, titania, zirconia and mixtures thereof,
   wt. % with respect to the weight of Paste B.

10. The kit of parts according to claim 1, neither Paste A nor Paste B comprising at least one or more or all of the following components:
    polymerizable component(s) in an amount above 1 wt. %;
    initiator component(s) suitable to cure polymerizable component(s) in an amount above 1 wt. %;
    2-hydroxyethyl cellulose, sodium alginate, or sodium carboxymethyl cellulose in an amount above 0.5 wt. %;
    wt. % with respect to the weight of the respective Paste A or Paste B.

11. A process of producing a glass ionomer composition, the process comprising the step of mixing Paste A and Paste B of the kit of parts described in claim 1.

12. A hardened glass ionomer composition for dental use, the hardened composition being obtainable or as obtained by mixing Paste A and Paste B of the kit of parts described in claim 1 and letting the mixture harden,
the hardened glass ionomer composition being characterized by the following parameters in combination:
flexural strength: above 20 MPa determined according to EN-ISO 9917-2:2010 with the proviso that for covering the composition a glass slab is used instead of a foil;
compressive strength: above 100 MPa determined according to EN-ISO 9917-1:2007 with the proviso that for covering the composition a glass slab is used instead of a foil.

13. The hardened glass ionomer composition as described in claim 12, or the kit or parts as described in claim 1 for use as or for preparing a dental cement, dental filling material, dental core build up material or dental root channel filling material.

14. The kit of parts according to claim 1 wherein the acid-reactive filler A is selected from aluminosilicate glasses and fluoroaluminosilicate glasses.

15. The kit of part according to claim 1, wherein the Paste B contains a complexing agent characterized by the following features alone or in combination:
solubility: soluble in water (at least 50 g/l water at 23° C.);
molecular weight: from 50 to 500 g/mol, or from 75 to 300 g/mol.

16. The kit of parts according to claim 15, wherein the Paste B contains a complexing agent selected from the group consisting of tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof.

* * * * *